United States Patent
Martin et al.

(10) Patent No.: US 6,900,173 B2
(45) Date of Patent: *May 31, 2005

(54) PERIOPERATIVE MULTIVITAMIN PROTEIN BAR FOR USE IN PREPARING AN INDIVIDUAL FOR FAST SURGICAL RECOVERY

(76) Inventors: Kenneth A. Martin, 8907 Kanis Rd., Suite 330, Little Rock, AR (US) 72205; Teresa Leigh Barr, P.O. Box 1500, Port Townsend, WA (US) 98368

( * ) Notice: Subject to any disclaimer, the term of this patent is extended or adjusted under 35 U.S.C. 154(b) by 0 days.

This patent is subject to a terminal disclaimer.

(21) Appl. No.: 10/725,609

(22) Filed: Dec. 2, 2003

(65) Prior Publication Data

US 2004/0253295 A1 Dec. 16, 2004

Related U.S. Application Data

(63) Continuation-in-part of application No. 10/241,542, filed on Sep. 11, 2002, now Pat. No. 6,660,308.

(51) Int. Cl.⁷ .......................... A61K 31/00; A23C 9/12; A23J 1/00
(52) U.S. Cl. .......................... 514/1; 514/167; 514/251; 514/276; 514/458; 514/725; 426/63; 426/72; 426/73; 426/656
(58) Field of Search ............................ 514/1, 167, 251, 514/276, 458, 725; 426/63, 72, 73, 656; 435/184

(56) References Cited

U.S. PATENT DOCUMENTS

| | | |
|---|---|---|
| 3,686,406 A | 8/1972 | Sherlock ...................... 424/266 |
| 4,616,039 A | 10/1986 | Herschler .................... 514/711 |
| 4,621,137 A | 11/1986 | Miyake et al. ................. 536/5 |
| 5,827,834 A | 10/1998 | Falk et al. ..................... 514/54 |
| 5,852,002 A | 12/1998 | Falk et al. ..................... 514/54 |
| 5,916,565 A | 6/1999 | Rose et al. ................... 424/756 |
| 5,929,048 A | 7/1999 | Falk et al. ..................... 514/54 |
| 5,932,560 A | 8/1999 | Falk et al. ..................... 514/54 |
| 6,194,392 B1 | 2/2001 | Falk et al. ..................... 514/54 |
| 6,358,526 B1 | 3/2002 | Mergens et al. ............ 424/464 |
| 6,399,093 B1 | 6/2002 | Petrus ........................ 424/448 |

*Primary Examiner*—Elli Peselev
(74) *Attorney, Agent, or Firm*—Wendy Buskop; Buskop Law Group, P.C.

(57) ABSTRACT

The perioperative multivitamin protein bar for promoting an anabolic state in a person is made of from about 250 mg to about 2500 mg of a digestive enzyme, such as bromelain, pepsin, amylase, protease, lipase, cellulase, lactase, alpha-g, glucoamylase, invertase, malt diastase, pectinase, xylanase, bromelain, betain, trypsin, or combinations thereof; from about 50 mg to about 2500 mg of an amino acid; from about 200 mg to about 2000 mg of a sea plant; from about 10 mg to about 8000 mg of a flavoring; from about 100 mg to about 2500 mg of Vitamin A, Vitamin B, Vitamin D, Vitamin E, Vitamin K, calcium, complexes thereof, or combinations thereof; and from about 1000 mg to about 9000 mg of a fiber.

16 Claims, No Drawings

PERIOPERATIVE MULTIVITAMIN PROTEIN BAR FOR USE IN PREPARING AN INDIVIDUAL FOR FAST SURGICAL RECOVERY

The present application is CIP and claims priority to U.S. patent application Ser. No. 10/241,542 filed on Sep. 11, 2002 and issued as U.S. Pat. No. 6,660,308, on Dec. 9, 2003.

FIELD

Embodiments relate to a perioperative multivitamin and protein bar used to make a person stronger so they can heal faster from surgery. Surgery is a medical treatment that involves operations or manipulations of a patient's body and usually cutting the body open to perform the task of surgery.

BACKGROUND

The success of a surgery can be dependant on many factors. The main factor being the overall health of the patient, which determines how well the patient will recover. Embodiments herein provide a healthful multivitamin protein bar to help strengthen the immune system. The protein bar also provides optimum nutritional amounts of essential vitamins, minerals, enzymes and acidophilus to aid a patient in recovering from the surgery as well as the adverse effects of anesthesia, antibiotics and the like.

Since many people do not have a proper dietary intake on a daily basis of the desired components, the present embodiments help insure adequate nutrition. In addition, others who may be healthy and take vitamin supplements may not have the desired perioperative health and support necessary for recovery.

SUMMARY

The perioperative multivitamin protein bar is usable for enhancing the immune system; chelating heavy metals from the blood; detoxifying the body; promoting tissue healing; increasing oxygenation of the blood; increasing gastrotrich motility to decrease constipation caused by narcotics, analgesics and anesthesia; and promoting healthy intestinal flora which reduces the harm from antibiotics and increases regularity.

The perioperative multivitamin protein bar contemplates using a unique and specific protein for detoxification to stabilize platelet function and regulate excessive bleeding and provide adequate protein. The perioperative multivitamin protein bar is to be consumed by a patient of average health two times a day for a period time of fourteen days prior to and after surgery.

The perioperative multivitamin protein bar for promoting an anabolic state in a person is made of from about 250 mg to about 2500 mg of a digestive enzyme, such as bromelain, pepsin, amylase, protease, lipase, cellulase, lactase, alpha-g, glucoamylase, invertase, malt diastase, pectinase, xylanase, bromelain, betain, trypsin, or combinations thereof; from about 50 mg to about 2500 mg of an amino acid; from about 200 mg to about 2000 mg of a sea plant; from about 10 mg to about 8000 mg of a flavoring; from about 100 mg to about 2500 mg of Vitamin A, Vitamin B, Vitamin D, Vitamin E, Vitamin K, calcium, complexes thereof, or combinations thereof; and from about 1000 mg to about 9000 mg of a fiber.

DETAILED DESCRIPTION OF THE PREFERRED EMBODIMENTS

Before explaining the present composition in detail, it is to be understood that the composition is not limited to the particular embodiments and that it can be practiced or carried out in various ways.

The protein bar is for a perioperative multivitamin protein bar in an anabolic formula for optimum recovery after surgery. Anabolic is used to describe a metabolic process in which energy is used to construct complex molecules from simpler ones. The protein bar is unique, as it supplies nutritional support before and after surgery to increase recovery times and promote health and wellness. The protein bar contemplates variations in the dosage amounts.

The perioperative multivitamin protein bar preferably has from about 200 mg to about 2000 mg of protein. Examples of proteins contemplated are whey proteins, soy or vegetable protein, urea, caseins and calcium caseinate, sodium caseinate protein, legume proteins, blue green micro algae proteins, nut and seed proteins and fish and animal proteins derived from eggs, meat or milk and combinations thereof. Bluegreen micro-algae form spiral filaments or chains that as a dietary supplement that contain 65% protein in the dried state.

Additionally, the protein bar can have from about 10 mg to about 8000 mg of a flavoring extract, such as syrup or sugar. The flavorings can be natural or artificial or alone or in combinations.

Various vitamins can be used. The protein bar can include from about 100 mg to about 2500 mg of Vitamin B, Vitamin C, Vitamin E, zinc oxide, copper gluconate and potassium, or complexes of these vitamins.

If Vitamin B is used, the preferred dosage is from about 10 mg to about 500 mg Vitamin B. The preferred Vitamin B is a Vitamin B complex, The Vitamin B complex includes thiamine (Vitamin B1), riboflavin (Vitamin B2), niacin (Vitamin B3), pyridoxine (Vitamin B6), folic acid (Vitamin B9), cyanocobalamin (Vitamin B12), pantothenic acid, and biotin. The Vitamin B family aid metabolic activity and also produces energy. The Vitamin B family is also involved in making red blood cells that carry oxygen throughout the body and is necessary for every part of the body to work properly.

If Vitamin C is used, the preferred dosage is from about 250 mg to about 2,500 mg. Vitamin C comes in two basic forms: ascorbic acid and calcium ascorbates. Vitamin C is naturally found in citrus fruits, such as oranges, grapefruit, lemons, mangos, and the like, and in many green vegetables, such as asparagus, broccoli, spinach, green peppers, and peas, tomatoes, potatoes and cabbage. Ascorbic acid is the standard form of vitamin C. Examples of Vitamin C usable in the invention are ascorbic acid, mineral ascorbates, calcium ascorbates, a potassium ascorbate with at least one threonate and combinations of these.

Vitamin C is one of several antioxidants and maintains collagen, a protein necessary for the formation of skin, ligaments and bones. Vitamin C also enhances the immune systems that helps heal wounds and mend fractures. Vitamin C also aids in resisting some types of bacterial and viral infections, as well as also aiding in the absorption of iron.

If Vitamin E is used, the preferred dosage is from about 50 mg to about 5000 mg. Vitamin E is an antioxidant that protects cell membranes and other fat-soluble parts of the body. Vitamin E also plays a role in the body's ability to process glucose. In the last ten years, studies have clarified the function of Vitamin E in the cells. In addition to its antioxidant functions, Vitamin E is now known to act through other mechanisms, including direct effects on inflammation, blood cell regulation, connective tissue growth, and genetic control of cell division, improve circulation, and allow the muscles to use oxygen. Vitamin E is found naturally in wheat germ oil, nuts and seeds, whole grains, egg yolks, and leafy green vegetables and certain vegetable oils. The names of all types of vitamin E begin with either d or dl, which refer to differences in chemical structure. The d form is natural and also known as RRR-alpha tocopherol and dl is a synthetic version, more correctly known as all-rac-alpha tocopherol. The natural form is more active and better absorbed by the body. Vitamin E is traditionally measured in international units (IU). 100 IU of Vitamin E requires about 67 mg of the natural form, but closer to 100 mg of the synthetic form.

The protein bar uses 67 mg for 100 IU of the preferable natural Vitamin E. The Vitamin E can be a tocopherol or tocopheryl followed by the name of what is attached to it, such as tocopheryl acetate. The most common forms of vitamin E are d-alpha tocopherol and d-alpha tocopheryl acetate or succinate and combinations or complexes thereof. The preferred Vitamin E is d-alpha tocopherol at 590 mg per dosage bar.

It is contemplated that the perioperative multivitamin protein bar includes from 250 mg to 15,000 mg of Vitamin A. Vitamin A is fat-soluble vitamin. Retinol is one of the most active, or usable, forms of vitamin A, and is found in animal products such as liver and eggs and can be converted to retinal and retinoic acid. Provitamin A carotenoids that are found in plant foods which contain darkly colored pigments which are converted to vitamin A. 26% to 34% of vitamin A consumed in the United States is provided by provitamin A carotenoids. Beta-carotene is a provitamin A carotenoid that is more efficiently converted to retinol than other carotenoids. The preferred Vitamin A is beta-carotene.

If Vitamin K is used, the preferred dosage is from about 10 mcg to about 150 mcg. Vitamin K is a generic term for derivatives of 2-methyl-1,4-naphthoquinone that have coagulation activity. Vitamin K's importance to the integrity of bones is essential. Vitamin K activates at least three proteins involved in bone health. Improved analytical methods show that the Vitamin K is not abundant in diet. The RDA of Vitamin K is 65 µg per day for adult females and 80 µg per day for adult males. Vitamin K adds chemical entities called carboxyl groups to osteocalcin and other proteins that build and maintain bone. Evidence exists that hip fractures may be associated with lower saturation of osteocalcin and that Vitamin K does create a positive effect on bone health, even for aging mammals.

If Vitamin D is used, the preferred dosage is from about 100 mcg to 600 mcg. The major biologic function of vitamin D is to maintain normal blood levels of calcium and phosphorus. Vitamin D aids in the absorption of calcium helping to form and maintain strong bones. Vitamin D promotes bone mineralization in conjunction with other vitamins and minerals. Vitamin D also prevents bones from becoming thin, brittle, and soft.

The protein bar can also include an amount of a binder, such as from about 1.0 weight percent to about 25.0 weight percent of a fat. The fat can be a saturated fat, a polysaturated fat, a monosaturated fat, a hydrogenated fat, a polyunsaturated fat, or an Omega 3 fatty acid. Saturated fats are solids at room temperature and turn to oil when heated. Most saturated fats are come from meat, poultry, and dairy products. Polyunsaturated fats originate from plant sources and are liquid at room temperature, such as vegetable oils from safflower, sunflower, sesame, cottonseed, corn oil and the like. Monounsaturated fats include olive oil, canola, and peanut oil and help decrease the LDL levels of cholesterol. Hydrogenated fats begin as liquid fats but are solidified when hydrogen atoms are added. Most hydrogenated fats are partially hydrogenated vegetable oils. Monosaturated fats are the preferred fats to be used as a binder.

Omega 3 fatty acids also aid in the perioperative multivitamin protein bar to lower cholesterol and triglyceride levels and reduce the risk of blood clot formation. Omega 3 fatty acids are essential fatty acids that our bodies cannot make by themselves and must be obtained from the food that we eat. Fish oils, derived from mackerel, lake trout, herring, sardines, albacore tuna and salmon, are also high in two kinds of Omega-3 fatty acids: eicosapentaenoic acid and docosahexaenoic acid.

Omega-3 fatty acids from plant sources include tofu and other forms of soybeans, canola, walnut and flaxseed. Their oils also contain alpha-linolenic acid, another form of omega-3 fatty acid. Omega 3 fatty acids used in the protein bar can also be derived from pumpkin seeds, almonds, sesame seeds, walnuts, or combinations of these fatty acids.

From about 1000 mg to about 9000 mg of fiber can be used in the protein bar. Fiber is the elongated, threadlike structures in fruits, vegetables, and grains that cannot be digested. Fiber has long been recognized as one of the best food ingredients for maintaining bowel regularity and preventing constipation.

The two types of fiber are water-soluble and insoluble. Water-soluble fiber dissolves in water and is found in oat bran, legumes, psyllium, nuts, beans, pectins, and various fruits and vegetables. Water-soluble fiber forms a bulky gel in the intestine that regulates the flow of waste materials through the digestive tract. Insoluble fiber cannot be dissolved in water, meaning that our bodies cannot digest it. Insoluble fiber includes the undissolvable parts of plant walls and is found in greatest amounts in cereals, brans, and vegetables. The primary function of insoluble fiber is to collect water that increases stool bulk in the large intestine. Soluble and insoluble fiber can be used alone or in combination.

The protein bar in still another embodiment can include flavoring additives such as natural and artificial extracts, sweeteners, sugars, syrups and flavorings in portions from about 250 mg to about 5,000 mg.

The syrups used in the protein bar can be selected for the following list: molasses, maple syrup, honey, corn syrup, high fructose corn syrup and inverted sugar. Molasses is a viscous liquid, containing sucrose, invert sugar, minerals and color, which is a by-product of sugar refining. Maple syrup is prepared from the sap of maple trees by boiling and evaporating to reduce the moisture content. Honey is a mixture of glucose and fructose that is collected from beehives. Corn syrup is glucose syrup that is made from the acid or enzyme hydrolysis of cornstarch. High fructose corn syrup results from enzyme hydrolysis of corn syrup to produce a product with 55–90% fructose. Invert sugar is formed from the partial or complete hydrolysis of sugar using heat, water and acid and/or invertase enzyme.

Artificial sweeteners can be used in the supplemental protein bar. Examples of artificial sweeteners are aspartamane, sucralose and acesulfamine-K. Most artificial sweeteners are generally hundreds of times sweeter than sugar, and provide sweetening without calories. Aspartame is approximately two hundred times sweeter than sucrose. Acesulfame-K is two hundred times sweeter than sucrose and does not break down with heat, but requires the addition of some sucrose or other sweeteners to reduce its bitter, metallic flavor that may occur. Sucralose is produced by the selective chlorination of the sucrose molecule. Sucralose is six hundred times sweeter than sugar and is free of calories. Saccharine is produced artificially by the oxidation of a sulphamic derivative of toluene. Saccharine is one of the sweetest substances known with over two hundred times the sweetening power of sugar.

Examples of usable sugars include dextrose, maple sugar, cane sugar, beet sugar, a fructose, a sucrose, raw sugar, brown sugar, granulated sugar, glucose, maltose, lactose and combinations of these sugars. Granulated sugar can be extracted from both sugar cane and sugar beets.

Raw sugar is not fully refined and usually contains about 97% sucrose and 3% non-sugar compounds. Treating white sugar crystals with molasses syrup and blending the mix prepare brown sugar. Sucrose or table sugar is a disaccharide that is composed of one glucose molecule and one fructose molecule. Sucrose can be broken down into two monosaccharides, glucose and fructose. Glucose is a sweetener that is less sweet than sucrose. Fructose is sweeter than sucrose. Maltose is a disaccharide that is derived from the hydrolysis of starch by amylase. Maltose is produced during the malting of grains, especially barley. Lactose is a disaccharide that is present in milk.

Flavorings can be added to the protein bar, such as a raspberry flavoring, chocolate flavoring, vanilla flavoring, strawberry flavoring, apple flavoring, citrus flavoring, kiwi flavoring, banana flavoring, coconut, caramel flavoring, grape flavoring, blueberry flavoring, peanut and nut butters, almond flavoring, tart cherry flavoring, coffee flavoring, cinnamon, ginger, nutmeg, clove, ginger, peach flavoring, pear flavoring, or other herbs, nuts and fruits.

The perioperative multivitamin protein bar could also include a fruit ingredient, a nut ingredient, and a vegetable ingredient.

The fiber usable in the perioperative multivitamin protein bar can be a nutritional grain. Examples of usable grains are quinoa, millet, spelt, buckwheat, kamut, corn, rice, wheat, barley, oats, amaranth, wheat, bulgur, rye and combinations of these grains.

Other additives can be used in the protein bar, such as from about 50 mg to about 800 mg of a naturally produced sulfur compound like s-adenosylmethionine. The body manufactures s-adenosylmethionine from methionine, an amino acid found in protein-rich foods, and adenosine triphosphate, an energy-producing compound found in all cells. The s-adenosylmethionine molecule or a methyl group attaches itself to tissues and organs in the body providing a critical link in methylation. Methylation is a chemical reaction that occurs billions of times a second throughout the body, thereby promoting cell growth.

In a preferred embodiment, the sulfur compound is methyl sulfonyl methane (MSM).

The protein bar can include minerals, such as from about 1 mg to about 500 mg of selenium, boron, manganese, magnesium and combinations thereof.

In still another embodiment, the protein bar can include from about 1 mg to about 20 mg of a digestive enzyme. Preferred digestive enzymes are bromelain, pepsin, amylase, protease, lipase, cellulase, lactase, alpha-g, glucoamylase, invertase, malt diastase, pectinase, xylanase, bromelain, betain, and trypsin. These digestive enzymes can be in combinations or alone for aiding digestion.

Enzymes help break down food proteins, carbohydrates, and lipids. Mammals digest all their food extra-cellularly. Digestive enzymes are secreted from cells lining the inner surfaces of the exocrine glands. The enzymes hydrolyze the macromolecules in food into small, soluble molecules that can be absorbed into cells.

The perioperative multivitamin protein bar can contain from about 1 billion to about 20 billion probiotics. Studies show that a correlative link exists between enhanced immune protection and probiotic bacteria. Probiotic microflora help reduce infections, maintain intestinal microflora balance, directly inhibit pathogenic bacteria in the intestine by competing for nutrients as well as space, and create a low-pH environment for pathogenic and putrefactive bacteria by producing organic acids, such as lactic acid, acetic acid, and propionic acid.

Probiotics also produce natural antibiotics, such as acidolin, acidophilin, bulgaricin, and plantaricin or bacteriocines, and other substances that inhibit the growth of pathogens. Probiotic bacteria modulate host defense mechanisms by affecting both nonspecific and gut-associated immune functions. Probiotics also affect the production of IgA-producing cells and enhance levels of interferon-alpha and polymorphonuclear cell phagocytic capacity. Probiotic bacteria can also suppress inflammatory response and help control intestinal inflammatory diseases. Numerous species of lactobacilli and bifidobacteria exist, but the main species with probiotic characteristics are L. casei, B. lactis, L. johnsonii, B. breve, L. bulgaricus, B. animalis, L. rhamnosus, B. infantis, L. reuteri, B. longum, and L. acidophilus.

In another embodiment, the perioperative multivitamin protein bar can contain sea plants, such as seaweeds, grasses, and algae that have detoxification properties to remove impurities in the bloodstream. The protein bar can contain from about 1 gram to about 25 grams of the sea plants. Examples of the sea plants are seaweeds, grasses, algae, blue green algae, chlorella, kelp, spirulina, wheat grass, barley grass, fucus gardneri, ulva latuca, alaria valida, nereocystis luetkeana, laminaria, ulva linza, gigarina, costaria costata, phodymenia pertusa, dead sea minerals, and combinations thereof.

Additionally, calcium can be included in the perioperative multivitamin protein bar in a portion from about 250 mg to about 1500 mg. Calcium may be used in the form of calcium carbonate, calcium citrate, calcium lactate, calcium gluconate and combinations thereof.

Amino acids can be used in the perioperative multivitamin protein bar in amounts of 50 mg to 2500 mg. Amino acids build cells and repair tissue and form antibodies to combat invading bacteria and viruses. Amino acids are part of the enzyme and hormonal system, build nucleoproteins, carry oxygen throughout the body and participate in muscle activity. When proteins are broken down by digestion, the result of the digestion is twenty-two amino acids. Eight amino acids are essential and cannot be manufactured by the body. The remaining amino acids are non-essential and can be manufactured by the body. Amino acids usable with the protein are tryptophan, lysine, methionine, phenylalaine, threonine, valine, leucine & isoleucine, arginine, tyrosine, glycine, serine, glutamic acid, aspartic acid, taurine, cystine, histidine, proline, and alanine. The amino acids can be used alone or in combination with one another.

The protein bar can be prepared by baking, cooking, cold processing, micro-waving, or extrusion (an extruded bar).

The protein bar can also include flavorings of fruit juice, vegetable juice, blends of juice, juice and concentrates of juice.

The preferred composition of a 70-gram protein bar is as follows:

| Ingredient | Wt/% |
| --- | --- |
| Probiotic bacteria | 2.00 |
| S-adenosylmethionine | 0.28 |
| Nutritional Grains | 3.0 |
| Digestive Enzymes | 0.20 |
| Spirulina | 5.84 |
| Soy protein concentrate | 12.58 |
| Fiber | 6.0 |
| 90% high fructose corn syrup | 10.13 |
| Vitamin Complex | 27.0 |
| Partially hydrogenated soybean oil and Fatty Acids | 0.34 |
| Honey | 4.39 |
| Water | 9.80 |
| Flavor powder | 3.89 |
| Flavoring | 0.69 |
| Citric acid | 2.21 |
| Aspartame | 0.44 |
| Potassium sorbate | 0.19 |
| Sodium acid pyrophosphate | 0.49 |
| Sorbitol | 2.68 |
| Polydextrose | 7.85 |

Preferably, the vitamin complex in the preferred composition is made of 250 mg of a Vitamin B complex (niacin, calcium pantothenate, pyridoxine hydrochloride (Vitamin-B6), riboflavin (Vitamin-B2), Thiamin Hydrochloride (Vitamin-B1), folic acid, biotin, Vitamin B12); 500 mg of a Vitamin C complex (calcium ascorbate and threonate); 590 mg of a Vitamin E complex (d-alpha tochopheryl or tocopherol); 61.5 mg of a minerals complex (selenium 50mg, boron 1.5, manganese 10 mg); 300 mg of a Bioflavonoid Complex (quercetin/100 mg and grapeseed extract 200 mg); 15,000 mg of Beta Carotene; 500 mg of Calcium Lactate; 75 mg of Vitamin K; and 1,500 mg of amino acids.

To manufacture the bar, the sorbitol and flavoring powders are sifted through a fine mesh screen separately. The flavoring is blended with about 8.0% of the corn syrup until they are mixed thoroughly. The rest of the corn syrup is then blended with the flavor mixture for about 1 minute. The soy protein concentrate and the polydextrose are then added to the oil mixture and blended for 1 minute. The honey and sorbitol are then blended into the oil mixture for about 1 minute. The flavoring, and the aspartame, are then added to the corn syrup mixture and blended for about 1 minute. The spirulina is then added and blended for about 1 minute.

The manufacturing continues by pre-blending the corn syrup, honey and citric acid and adding the blend to the corn syrup mixture. The sodium acid pyrophosphate is then added and the resultant mixture blended for 3 minutes. The potassium sorbate is dissolved in the water at 60° C. along with the vitamin complex, s-adenosylmethionine and then the water is cooled and added to the mixture and blended for about 3 minutes. The digestive enzymes are added to the mixture and blended for 1 minute. The probiotics are added to the mixture and blended for one minute. The nutritional grains and fiber are added to the mixture and blended for 3 minutes. The resultant mixture is then preferably extruded and cut into bars weighing approximately 70 grams.

While this composition has been described with emphasis on the preferred embodiments, it should be understood that within the scope of the appended claims, the composition might be practiced other than as specifically described herein.

What is claimed is:

1. A perioperative multivitamin protein bar for promoting an anabolic state in a person, wherein the protein bar comprises:

a. from about 250 mg to about 2500 rug of a digestive enzyme selected from the group cxmsisting of bromelain, pepsin, amylase, protease, lipase, celluisse, lactose, alpha-g, glucoamnylase, invertase, malt diastase, pectinase, xylanase, bromelain, betain, trypsin, and combinations thereof;

b. from about 50 mg to about 2500 mg of an amino acid;

c. from about 200mg to about 2000mg of a sea plant selected from the group consisting of kelp, blue green algae, sea vegetables, sea weed, chorella, spirulina, wheat grass, barley grass, other non-toxic leafy plants from the sea, and combinations thereof;

d. from about 10 mg to about 8000 mg of a flavoring;

e. a protein selected from the group consisting of a whey protein, soy protein, sodium caseinate protein, legume protein, egg protein, and combinations thereof;

f. from about 100 mg to about 2500 mg of a vitamin selected from the group consisting of Vitamin A, Vitamin B, Vitamin D, Vitamin E, Vitamin K, calcium, complexes thereof, and combinations thereof; and g. from about 1000mg to about 9000 mg of a fiber.

2. The perioperative multivitamin protein bar of claim 1, further comprising from about 10 mg to about 20 mg of a fat.

3. The perioperative multivitamin protein bar of the fat claim 2, wherein the fat is selected from the group consisting of a saturated fat, a polysaturated fat, a monosaturated fat, a polyunsaturated fat, and combination thereof.

4. The perioperative multivitamin protein bar of claim 1, further comprising an essential fatty acid derived from a member of the group consisting of pumpkin seed, almonds, sesame seeds, walnuts, flax seed, soy bean derivatives, and combinations thereof.

5. The perioperative multivitamin protein bar of claim 1, further comprising from about 250 mg to 5000 mg of an artificial sweetener or a sugar.

6. The perioperative multivitamin protein bar of claim 5, wherein the artificial sweetener is selected from the group consisting of aspartame, saccharine, calcium saccharine, and combinations thereof.

7. The perioperative multivitamin protein bar the of claim 5, wherein the sugar is selected from the group consisting of dextrose, maple sugar, cane sugar, beet sugar, fructose, sucrose, and combinations thereof.

8. The perioperative multivitamin protein bar of claim 1, wherein said flavorings comprises; a raspberry flavoring, chocolate flavoring, vanilla flavoring, strawberry flavoring, apple flavoring, citrus flavoring, kiwi flavoring, banana flavoring, coconut, caramel flavoring, grape flavoring, blueberry flavoring, peanut, almond flavoring, tart cherry flavoring, coffee flavoring, cinnamon, ginger, nutmeg, clove, ginger, peach flavoring, pear flavoring, other herbs, and combinations thereof.

9. The perioperative multivitamin protein bar of claim 1, wherein the Vitamin A is beta carotine.

10. The perioperative multivitamin protein bar of claim 1, wherein the Vitamin B is selected from the group consisting of Vitamin B1, Vitamin B3, Vitamin B5, Vitamin B6, Vitamin B-12, and combinations thereof.

11. The perioperative multivitamin protein bar of claim 1, wherein the Vitamin E is selected from the group consisting of tocopherol, tocopheryl tocopheryl acetate, d-alpha tocopherol, d-alpha tocopheryl acetate, d-alpha tocopheryl succinate, complexes thereof, and combinations thereof.

12. The perioperative multivitamin protein bar of claim 1, wherein the fiber is a grain or a flax seed.

13. The perioperative multivitamin protein bar of claim 12, wherein the grain is selected from the group consisting of a corn, a rice, a wheat, a barley, oats, quinoa, and combinations thereof.

14. A perioperative multivitamin protein bar for promoting an anabolic state in a person, wherein the protein bar comprises:

a. from about 1 mg to about 20 mg of a digestive enzyme selected from the group consisting of bromelain pepsin amylase, protease lipase, cellulase, lactase, alpha-g, glucoamylase, invertase, malt diastase, pectinase, xylanase, bromelain, betain, trypsin, and combinations thereof;

b. from about 50 mg to about 2500 mg of an amino acid;

c. from about 200 mg to about 2000 mg of a sea plant selected from the group consisting of kelp, blue green algae, sea vegetables, sea weed, cholerella, spirulina, wheat grass, barley grass, other non-toxic leafy plants from the sea, and combinations thereof:

d. from about 10 mg to about 8000 mg of a flavoring;

e. a protein selected from the group consisting of a whey protein, say protein, sodium caseinate protein legume protein, egg protein, and combinations thereof;

f. from about 100 mg to about 2500 mg of vitamin selected from the group consisting of Vitamin A, Vitamin B, Vitamin D, Vitamin E, Vitamin K, calcium, complexes thereof, and combinations thereof; and g. from about 1000 mg to about 9000 mg of a fiber.

15. The perioperative multivitamin protein bar of claim 1, further comprising from about 250 mg to about 500 mg of calcium.

16. The perioperative multivitamin protein bar of claim 1, wherein the amino acids are selected from the group consisting of tryptophan, lysine, methionine, phenylalaine, threonine, valine, leucine & isoleucine, arginine, tyrosine, glycine, serine, glutamic acid, aspartic acid, taurine, cystine, histidine, proline, alanine, and combinations thereof.

* * * * *